United States Patent [19]
Guthrie, Jr. et al.

[11] Patent Number: 5,739,035
[45] Date of Patent: Apr. 14, 1998

[54] DETECTION OF ALKALI-SILICA REACTION SWELLING IN CONCRETE BY STAINING

[75] Inventors: George D. Guthrie, Jr.; J. William Carey, both of Santa Fe, N. Mex.

[73] Assignee: The Regents of the University of California, Los Alamos, N. Mex.

[21] Appl. No.: 745,118

[22] Filed: Nov. 7, 1996

[51] Int. Cl.$^6$ .................................................... G01N 21/91
[52] U.S. Cl. .............................. 436/28; 436/72; 436/79; 436/164
[58] Field of Search .................... 436/28, 25, 72, 436/79, 164, 166; 73/86, 762, 865.8

[56] References Cited

U.S. PATENT DOCUMENTS 5,656,075  8/1997  Gaidis et al. ........................ 106/737

OTHER PUBLICATIONS

French, W.J. et al "Alkali–aggregate Reactions and the Middle East" Concrete, vol. 10, No. 1, pp. 18–20 (Jan. 1976).

Poole, A.B. et al "A Staining Technique for the Identification of Sulphates in Aggregates and Concretes" Mineralogical Magazine, vol. 40, pp. 315–316 (1975).

Natesaiyer, K.C. et al "Further Study of An In–Situ Identification Method for Alkali–Silica Reaction Products in Concrete" Cement and Concrete Research, vol. 19, pp. 770–778 (1989).

K. Natesaiyer et al., "In Situ Identification of ASR Products In Concrete," Cement and Concrete Research 18, 455 (1988).

Richard Helmuth et al., "Alkali–Silica Reactivity: An Overview of Research," Strategic Highways Research Program SHRP–C–342, National Research Council, Washington, DC (1993).

A. Gabriel et al., "A Staining Method For the Quantitative Determination Of Certain Rock Minerals," Am. Mineral. 14, 290 (1929).

Edgar H. Bailey et al., "Selective Staining of K–Feldspars And Plagioclase On Rock Slabs And Thin Sections," Am. Mineral. 45, 1020 (1960).

*Primary Examiner*—Jeffrey Snay
*Attorney, Agent, or Firm*—Samuel M. Freund

[57] ABSTRACT

A method using concentrated aqueous solutions of sodium cobaltinitrite and rhodamine B is described which can be used to identify concrete that contains gels formed by the alkali-silica reaction (ASR). These solutions present little health or environmental risk, are readily applied, and rapidly discriminate between two chemically distinct gels; K-rich, Na—K—Ca—Si gels are identified by yellow staining, and alkali-poor, Ca—Si gels are identified by pink staining.

37 Claims, No Drawings

DETECTION OF ALKALI-SILICA REACTION SWELLING IN CONCRETE BY STAINING

The invention was made with government support under Contract No. W-7405-ENG-36 awarded by the U.S. Department of Energy to the Regents of The University of California. The government has certain rights in the invention.

FIELD OF THE INVENTION

The present invention relates generally to detection of structural weaknesses in concrete and, more particularly, to a method using sodium cobaltinitrite and rhodamine B for identifying gel formation in concrete from the alkali-silica reaction (ASR).

BACKGROUND OF THE INVENTION

The alkali-silica reaction (ASR) is a primary cause of premature degradation of concrete structures, particularly for highways, bridgedecks, runways, and sidewalks. Such degradation occurs throughout the world; however, some regions have more frequent occurrences. The reaction occurs between concrete pore water, some aggregate constituents (e.g., poorly crystalline silica phases), and alkali cations (Na and K) released by the cement and/or aggregate. As the alkali content of the pore water increases, dissolution of the silica phases increases, resulting in a release of silica to form the gel. Gel formation results in a volume increase, which causes internal pressure in the concrete and eventually forms fractures. This process can be exacerbated by freeze-thaw cycles and by salting of road surfaces. Thus, ASR products found in concrete may be understood as gelatinous silica, and its crystalline modifications, having adsorbed sodium, potassium and calcium ions.

Important steps in the control of ASR include the recognition of potentially reactive aggregates and early diagnosis of ASR-affected structures. For these and other reasons, it is important to identify the presence of ASR gel in a structure as early as possible. Current approaches to the identification of ASR in concrete rely heavily on petrographic analyses that are expensive and time-consuming (often requiring days or weeks before an answer is obtained).

Recently, the Federal Highways Administration (FWHA) endorsed a staining procedure that was initially proposed in "In Situ Identification Of ASR Products In Concrete" by K. Natesaiyer and K. C. Hover, Cement and Concrete Research 18, 455 (1988) and subsequently tested and refined as part of the Strategic Highways Research Program (SHRP), in "Alkali-Silica Reactivity: An Overview Of Research" by Richard Helmuth et al., SHRP-C-342, National Research Council, Washington, DC (1993). This procedure uses uranyl acetate $[(UO_2)^{++}(C_4H_6O_4)^=]$ to treat the concrete surface, whereupon the uranyl ion, $(UO_2)^{++}$, is adsorbed in areas where silica gel is present, replacing previously adsorbed $Na^+$, $K^+$ or $Ca^{++}$ ions and may be detected by its yellow-green fluorescence under ultraviolet (UV) light.

The uranyl-acetate technique presents several disadvantages. Although the amounts of uranyl acetate employed are small, the technique results in a potential exposure to uranium which is hazardous as both a heavy metal and a radioactive element. Additionally, liquid and solid waste generated by this process is contaminated is with uranium, so disposal as mixed waste is costly. Due to the small amounts of uranium used in a typical test, disposal of the materials in the sewer system is attractive. However, this approach unnecessarily adds to system contamination. The use of the uranyl-acetate method also requires a source of UV radiation and a light-tight enclosure for viewing the fluorescence generated by adsorbed uranyl species, making the application of this procedure difficult in a field situation where the use of light-tight enclosures limits the area under investigation, and rendering the observation of a typical road surface tedious and slow.

A method for differentially staining K-feldspar (yellow) and plagioclase feldspar (red) on slab surfaces or uncovered thin sections is described in "Selective Staining of K-Feldspars And Plagioclase On Rock Slabs And Thin Sections," by Edgar H. Bailey and Rollin E. Stevens in Am. Mineral. 45, 1020 (1960). K-feldspar is stained yellow using sodium cobaltinitrite according to the method described in "A Staining Method For the Quantitative Determination Of Certain Rock Minerals," by A. Gabriel and E. P. Cox in Am. Mineral. 14, 290 (1929). The feldspar is first treated by etching the surface to be stained with hydrofluoric acid vapor to form etch residues, since such residues are subsequently stained, whereas the feldspar itself is not visibly stained. Residual potassium from the K-feldspar reacts with the sodium cobaltinitrite to form yellow potassium cobaltinitrite. Staining of plagioclase is accomplished by replacing the calcium ion in the etched feldspar with barium from barium chloride solution, which reacts with the rhodizonate reagent subsequently applied to form red insoluble barium rhodizonate.

Accordingly, it is an object of the present invention to provide a selective process for identifying concrete containing gels formed by the alkali-silica reaction.

Another object of the invention is to provide a selective process for identifying concrete containing gels formed by the alkali-silica reaction that uses environmentally benign chemicals.

Yet another object of the present invention is to provide a selective process for identifying concrete containing gels formed by the alkali-silica reaction that uses environmentally benign chemicals and does not require chemical pretreatment of the concrete.

Still another object of the invention is to provide a selective process for identifying concrete containing gels formed by the alkali-silica reaction that uses environmentally benign chemicals, that does not require chemical pretreatment of the concrete, and that does not require a fluorescence-excitation light source.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

To achieve the foregoing and other objects, and in accordance with the purposes of the present invention, as embodied and broadly described herein, the method for identifying concrete containing gels formed by the alkali-silica reaction hereof includes the steps of: contacting the surface of the concrete under investigation with a concentrated aqueous solution of sodium cobaltinitrite for a chosen period of time; contacting the surface of the concrete under investigation with a concentrated aqueous solution of rhodamine B for a chosen period of time; rinsing the concrete so treated with water; and searching the rinsed surface of the concrete for regions of yellow staining and for regions of pink staining, whereby K—rich, Na—K—Ca—Si gels generated from the alkali-silica reaction are identified by yellow staining and alkali-poor, Ca—Si gels generated from the alkali-silica reaction are identified by pink staining.

Preferably, the step of contacting the surface of the concrete under investigation with a concentrated aqueous solution of sodium cobaltinitrite for a chosen period of time occurs before the step of contacting the surface of the concrete under investigation with a concentrated aqueous solution of rhodamine B for a chosen period of time.

It is also preferred that the concrete under investigation be permitted to dry after the application of the solutions before viewing the staining.

Benefits and advantages of the present invention include selectivity for two types of gels produced by the alkali-silica reaction, the use of environmentally benign chemicals, the absence of a requirement for chemical pretreatment of the concrete, and the absence of a requirement for a fluorescence-excitation light source.

DETAILED DESCRIPTION

Briefly, the present invention includes the sequential application of solutions of each of two water soluble compounds to the concrete under investigation. Concentrated solutions of sodium cobaltinitrite and rhodamine B in water are prepared. The exact amounts of solutes are unimportant, but best results were obtained when the final solutions have undissolved solid. The concrete surface to be examined is treated by pre-rinsing with water and subsequently applying each solution to the surface. After 30–60 seconds, the concrete is rinsed thoroughly with water. The treated surface will show yellow and pink regions where ASR gel is present. Yellow regions indicate the presence of K-rich, Na—K—Ca—Si gels, while pink regions indicate alkali-poor gels. The final rinse step is required, since the yellow sodium cobaltinitrite solution will coat the entire concrete surface as will the pink rhodamine B solution, thereby obscuring the stained gel regions. Best results are obtained when the sample is treated first with the sodium cobaltinitrite solution; however, the application of the rhodamine B solution first gives adequate results. Moreover, although solutions containing both sodium cobaltinitrite and rhodamine B were found to selectively identify K-rich and alkali-poor gels, respectively, the intensity of the staining appears to be reduced from that produced when the individual solutions are used. The visibility of the colors improves as the concrete dries, and a previously treated sample may be re-treated with either solution to enhance the intensity of any staining already present. It has been observed that the staining intensity fades over the course of days to weeks. However, restaining the sample according to the method of the present invention restores the original intensity.

Having generally described the invention, the following examples illustrate more detailed characteristics thereof.

EXAMPLE 1

A concrete chip was broken off from a concrete core. The chip was placed in a beaker containing a concentrated sodium cobaltinitrite solution in water for approximately 1 min., removed, and subsequently rinsed with water. The chip was then placed in a beaker containing rhodamine B solution for approximately 1 min., removed, and rinsed with water. After drying with an air gun, the concrete chip exhibited a pink hue over large regions of the paste surface and a yellow hue in isolated pockets and in rings circling some aggregate particles. Upon examination using a binocular microscope, it was apparent that both the pink and yellow regions involved gels which showed shrinkage cracking. Examples of both gels were extracted from the concrete and prepared for examination by scanning electron microscopy which showed Na, Si, K, Ca, and Co in the yellow stained gel (the Co resulting from the sodium cobaltinitrite), and Si and Ca in the pink stained gel. Since scanning electron microscopy cannot detect hydrogen and the detector employed does not detect oxygen or nitrogen, the elements set forth in the previous sentence were the only elements observed. The concrete sample was also examined petrographically in order to verify the presence of ASR gel the location of which was found to be consistent with the staining results.

EXAMPLE 2

A concrete chip was broken from a concrete core. The chip was placed in a beaker containing a concentrated solution of sodium cobaltinitrite in water for approximately 1 min., removed, and subsequently rinsed with water. The chip was then placed in a beaker of rhodamine B solution for about 1 minute, removed and subsequently rinsed with water. After drying with an air gun, the concrete chip exhibited a yellow hue in isolated pockets and in rings circling some aggregate particles. No regions of pink staining were observed. Upon examination using a binocular microscope, it was apparent that both the yellow regions contained a gel that showed shrinkage cracking.

EXAMPLE 3

A core was taken from a concrete structure apparently affected by ASR. The core was treated immediately in the field using the procedure set forth hereinabove, and was found to test positive for yellow ASR gel but negative for pink ASR gel. The core was subsequently examined petrographically to confirm the presence of ASR gel, the is location of which was consistent with the staining results.

EXAMPLE 4

A core was removed form a section of road showing no apparent signs of significant distress. The core was treated in the field using the method of the present invention, but showed no signs of yellow or pink gel. Yellow and pink patches were observed at locations where gravel has become dislodged from the concrete surface.

EXAMPLE 5

A core was removed from a concrete structure apparently affected by ASR. The core was treated using the method of the present invention except that a single solution was prepared which contained both sodium cobaltinitrite and rhodamine B. The treated core showed both yellow and pink gel following rinsing. However, the intensity of the staining appeared to be less dramatic than that which results from sequential staining using individual concentrated solutions.

The foregoing description of the invention has been presented for purposes of illustration and description and is not intended to be exhaustive or to limit the invention to the precise form disclosed, and obviously many modifications and variations are possible in light of the above teaching. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. A method for identifying concrete containing gels formed by the alkali-silica reaction comprising the steps of:
   a. contacting the surface of the concrete under investigation with a concentrated aqueous solution of sodium cobaltinitrite for a chosen period of time;
   b. rinsing the treated concrete surface with water; and
   c. searching the rinsed surface of the concrete for regions of yellow staining, whereby K-rich, Na—K—Ca—Si gels generated from the alkali-silica reaction are identified by yellow staining.

2. The method for identifying concrete containing gels formed by the alkali-silica reaction as described in claim 1, wherein the chosen period of time for contacting the concrete under investigation with the concentrated solution of sodium cobaltinitrite is between 30 and 60 seconds.

3. The method for identifying concrete containing gels formed by the alkali-silica reaction as described in claim 1, wherein the concentrated solution of sodium cobaltinitrite is a saturated solution thereof.

4. The method for identifying concrete containing gels formed by the alkali-silica reaction as described in claim 3, wherein the saturated solution of sodium cobaltinitrite contains undissolved sodium cobaltinitrite.

5. The method for identifying concrete containing gels formed by the alkali-silica reaction as described in claim 1, further comprising the step of rinsing the concrete under investigation with water before said step of contacting the surface thereof with the concentrated solution of sodium cobaltinitrite.

6. The method for identifying concrete containing gels formed by the alkali-silica reaction as described in claim 5, further comprising the step of permitting the concrete to dry after said step of rinsing the concrete surface with water after said step of contacting the concrete with the concentrated solution of sodium cobaltinitrite and before said step of searching the treated concrete surface for regions of yellow staining.

7. The method for identifying concrete containing gels formed by the alkali-silica reaction as described in claim 1, further comprising the steps of contacting the surface of the concrete under investigation with a concentrated aqueous solution of rhodamine B for a chosen period of time, after said step of rinsing the concrete treated with the concentrated aqueous solution of sodium cobaltinitrite, rinsing the concrete surface treated with the concentrated aqueous solution of rhodamine B with water, and searching the rinsed surface of the concrete for regions of pink staining, whereby alkali-poor, Ca—Si gels generated from the alkali-silica reaction are identified by pink staining.

8. The method for identifying concrete containing gels formed by the alkali-silica reaction as described in claim 7, further comprising the step of rinsing the concrete under investigation with water before said step of contacting the surface thereof with the concentrated solution of sodium cobaltinitrite.

9. The method for identifying concrete containing gels formed by the alkali-silica reaction as described in claim 7, further comprising the step of permitting the concrete to dry after each of said steps of rinsing the concrete surface with water after each of said steps of contacting the concrete with the concentrated solutions of sodium cobaltinitrite and rhodamine B and before each of said steps of searching the treated concrete surface for regions of yellow and pink staining, respectively.

10. The method for identifying concrete containing gels formed by the alkali-silica reaction as described in claim 7, wherein the chosen period of time for contacting the concrete under investigation with the concentrated solution of rhodamine B is between 30 and 60 seconds.

11. The method for identifying concrete containing gels formed by the alkali-silica reaction as described in claim 7, wherein the concentrated solution of rhodamine B is a saturated solution thereof.

12. The method for identifying concrete containing gels formed by the alkali-silica reaction as described in claim 11, wherein the saturated solution of rhodamine B contains undissolved rhodamine B.

13. A method for identifying concrete containing gels formed by the alkali-silica reaction comprising the steps of:
   a. contacting the surface of the concrete under investigation with a concentrated aqueous solution of sodium cobaltinitrite for a chosen period of time;
   b. contacting the surface of the concrete under investigation with a concentrated aqueous solution of rhodamine B for a chosen period of time;
   c. rinsing the treated concrete surface with water; and
   d. searching the rinsed surface of the concrete for regions of yellow staining and for regions of pink staining, whereby K-rich, Na—K—Ca—Si gels generated from the alkali-silica reaction are identified by yellow staining and alkali-poor, Ca—Si gels generated from the alkali-silica reaction are identified by pink staining.

14. The method for identifying concrete containing gels formed by the alkali-silica reaction as described in claim 13, further comprising the steps of rinsing the concrete under investigation with water before each of said steps of contacting the surface thereof with the concentrated solution of sodium cobaltinitrite and the concentrated solution of rhodamine B.

15. The method for identifying concrete containing gels formed by the alkali-silica reaction as described in claim 13, further comprising the step of permitting the concrete to dry after said step of rinsing the concrete surface with water after the latter of said steps of contacting with the concentrated solution of sodium cobaltinitrite and contacting with the concentrated solution of rhodamine B and before said step of searching the treated concrete surface for regions of yellow and pink staining, respectively.

16. The method for identifying concrete containing gels formed by the alkali-silica reaction as described in claim 13, wherein the chosen period of time for contacting the concrete under investigation with the concentrated solution of sodium cobaltinitrite is between 30 and 60 seconds, and wherein the chosen period of time for contacting the concrete under investigation with the concentrated solution of rhodamine B is between 30 and 60 seconds.

17. The method for identifying concrete containing gels formed by the alkali-silica reaction as described in claim 13, wherein said step of contacting the surface of the concrete under investigation with a concentrated solution of sodium cobaltinitrite for a chosen period of time occurs before said step of contacting the surface of the concrete under investigation with a concentrated solution of rhodamine B for a chosen period of time.

18. The method for identifying concrete containing gels formed by the alkali-silica reaction as described in claim 13, wherein the concentrated solutions of sodium cobaltinitrite and rhodamine B are saturated solutions thereof.

19. The method for identifying concrete containing gels formed by the alkali-silica reaction as described in claim 18, wherein the saturated solution of sodium cobaltinitrite contains undissolved sodium cobaltinitrite and the saturated solution of rhodamine B contains undissolved rhodamine B.

20. A method for identifying concrete containing gels formed by the alkali-silica reaction comprising the steps of:
   a. contacting the surface of the concrete under investigation with a concentrated aqueous solution of rhodamine B for a chosen period of time;
   b. rinsing the treated concrete surface with water; and
   c. searching the rinsed surface of the concrete for regions of pink staining, whereby alkali-poor gels generated from the alkali-silica reaction are identified by pink staining.

21. The method for identifying concrete containing gels formed by the alkali-silica reaction as described in claim 20, wherein the chosen period of time for contacting the concrete under investigation with the concentrated solution of rhodamine B is between 30 and 60 seconds.

22. The method for identifying concrete containing gels formed by the alkali-silica reaction as described in claim 20, wherein the concentrated solution of rhodamine B is a saturated solution thereof.

23. The method for identifying concrete containing gels formed by the alkali-silica reaction as described in claim 22, wherein the saturated solution of rhodamine B contains undissolved rhodamine B.

24. The method for identifying concrete containing gels formed by the alkali-silica reaction as described in claim 20, further comprising the step of rinsing the concrete under investigation with water before said step of contacting the surface thereof with the concentrated solution of rhodamine B.

25. The method for identifying concrete containing gels formed by the alkali-silica reaction as described in claim 24, further comprising the step of permitting the concrete to dry after said step of rinsing the concrete surface with water after said step of contacting the concrete with the concentrated solution of rhodamine B and before said step of searching the treated concrete surface for regions of pink staining.

26. The method for identifying concrete containing gels formed by the alkali-silica reaction as described in claim 20, further comprising the steps of contacting the surface of the concrete under investigation with a concentrated aqueous solution of sodium cobaltinitrite for a chosen period of time, after said step of rinsing the concrete treated with the concentrated aqueous solution of rhodamine B, rinsing the concrete surface, treated with the concentrated aqueous solution of sodium cobaltinitrite with water, and searching the rinsed surface of the concrete for regions of yellow staining, whereby K-rich, Na—K—Ca—Si gels generated from the alkali-silica reaction are identified by yellow staining.

27. The method for identifying concrete containing gels formed by the alkali-silica reaction as described in claim 26, further comprising the step of rinsing the concrete under investigation with water before said step of contacting the surface thereof with the concentrated solution of rhodamine B.

28. The method for identifying concrete containing gels formed by the alkali-silica reaction as described in claim 26, further including the step of permitting the concrete to dry after each of said steps of rinsing the concrete surface with water after each of said steps of contacting the concrete with the concentrated solutions of rhodamine B and sodium cobaltinitrite and before each of said steps of searching the treated concrete surface for regions of pink and yellow staining, respectively.

29. The method for identifying concrete containing gels formed by the alkali-silica reaction as described in claim 26, wherein the chosen period of time for contacting the concrete under investigation with the concentrated solution of sodium cobaltinitrite is between 30 and 60 seconds.

30. The method for identifying concrete containing gels formed by the alkali-silica reaction as described in claim 26, wherein the concentrated solution of sodium cobaltinitrite is a saturated solution thereof.

31. The method for identifying concrete containing gels formed by the alkali-silica reaction as described in claim 30, wherein the saturated solution of sodium cobaltinitrite contains undissolved sodium cobaltinitrite.

32. A method for identifying concrete containing gels formed by the alkali-silica reaction comprising the steps of:
   a. contacting the surface of the concrete under investigation with a concentrated aqueous solution of sodium cobaltinitrite and rhodamine B for a chosen period of time;
   b. rinsing the treated concrete surface with water; and
   c. searching the rinsed surface of the concrete for regions of yellow staining and for regions of pink staining, whereby K-rich, Na—K—Ca—Si gels generated from the alkali-silica reaction are identified by yellow staining and alkali-poor, Ca—Si gels generated from the alkali-silica reaction are identified by pink staining.

33. The method for identifying concrete containing gels formed by the alkali-silica reaction as described in claim 32 further comprising the step of rinsing the concrete under investigation with water before said step of contacting the surface thereof with the concentrated solution of sodium cobaltinitrite and rhodamine B.

34. The method for identifying concrete containing gels formed by the alkali-silica reaction as described in claim 32, further comprising the step of permitting the concrete to dry after said step of rinsing the concrete surface with water after said step of contacting with the concentrated solution of sodium cobaltinitrite and rhodamine B and before said step of searching the treated concrete surface for regions of yellow and pink staining, respectively.

35. The method for identifying concrete containing gels formed by the alkali-silica reaction as described in claim 32, wherein the chosen period of time for contacting the concrete under investigation with the concentrated solution of sodium cobaltinitrite and rhodamine B is between 30 and 60 seconds.

36. The method for identifying concrete containing gels formed by the alkali-silica reaction as described in claim 32, wherein the concentrated solution of sodium cobaltinitrite and rhodamine B is a saturated solution thereof.

37. The method for identifying concrete containing gels formed by the alkali-silica reaction as described in claim 36, wherein the saturated solution of sodium cobaltinitrite and rhodamine B contains undissolved sodium cobaltinitrite and undissolved rhodamine B.

* * * * *